United States Patent [19]

Fischer, deceased

[11] 3,966,451

[45] June 29, 1976

[54] HERBICIDAL MIXTURES OF 3-LOWER ALKYL-2,1-3-BENZOTHIADIAZINONE-(4)-2,2-DIOXIDES OR SALTS THEREOF AND 1,1'-DI-(3,5-DIMETHYLMORPHOLINE-CARBONYLMETHYL)-4,4'-DIPYRIDYLIUM SALT

[75] Inventor: Adolf Fischer, deceased, late of Mutterstadt, Germany, by Caecilia Emma Fischer, legal representative

[73] Assignee: BASF Aktiengesellschaft, Ludwigshafen (Rhine), Germany

[22] Filed: Feb. 10, 1975

[21] Appl. No.: 548,386

Related U.S. Application Data

[62] Division of Ser. No. 432,687, Jan. 11, 1974, abandoned, which is a division of Ser. No. 343,629, March 22, 1973, Pat. No. 3,888,655.

[30] Foreign Application Priority Data

Apr. 13, 1972 Germany.......................... 2217722

[52] U.S. Cl........................................ 71/91; 71/94
[51] Int. Cl.²........................................ A01N 9/12
[58] Field of Search................................ 71/91, 94

[56] References Cited
UNITED STATES PATENTS 3,671,213   6/1972   White ..................................... 71/94
3,708,277   1/1973   Zeidler et al. ........................... 71/91

OTHER PUBLICATIONS

Fischer I, "Herbicidal Compositions" (1971) CA 74 No. 110714w (1971).
Fischer II, "Herbicidal Compositions" (1970) CA 74 No. 220602 (1971).
Fischer III, "Herbicidal Compositions, etc;" (1971) CA 75 No. 75217H (1971).

Primary Examiner—Glennon Hollrah
Attorney, Agent, or Firm—Johnston, Keil, Thompson & Shurtleff

[57] ABSTRACT

Herbicide compositions of mixtures in the weight ratio of 5:1 to 1:5 of (a) 3-lower alkyl-2,1,3-benzothiadiazinone-(4)-2,2-dioxide and (b) a compound of the formula

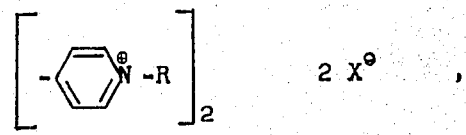

where R denotes the radical

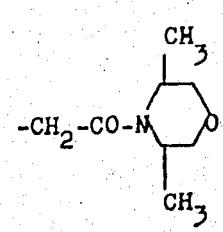

and X denotes an anion (Cl⁻, Br⁻, methyl sulfate).

10 Claims, No Drawings

HERBICIDAL MIXTURES OF 3-LOWER ALKYL-2,1-3-BENZOTHIADIAZINONE-(4)-2,2-DIOXIDES OR SALTS THEREOF AND 1,1'-DI-(3,5-DIMETHYLMORPHOLINE-CARBONYLMETHYL)-4,4'-DIPYRIDYLIUM SALT

RELATED APPLICATION

This application is a division of my copending application Ser. No. 432,687, filed Jan. 11, 1974 now abandoned, which in turn is a division of my application Ser. No. 343,629, filed Mar. 22, 1973 now U.S. Pat. No. 3,888,655, the disclosures of which are incorporated herein by reference.

The present invention relates to a herbicide comprising a composition of several active ingredients.

It is known that substituted phenyl ethers, carbamates, terephthalates, acid amides, benzoic acids, fluorenecarboxylic acids and benzothiadiazinones have a herbicidal action. However, this action is poor.

I have now found that a composition of
a. a compound of the formula

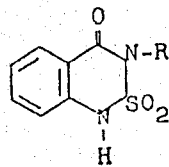

where R denotes lower alkyl of a maximum of 4 carbon atoms, or its salts, such as alkali metal, alkaline earth metal, ammonium, hydroxyalkylammonium, alkylammonium and hydrazine salts, e.g. salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and
b. a compound of the formula

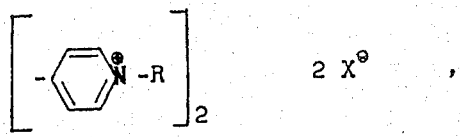

where R denotes the radical

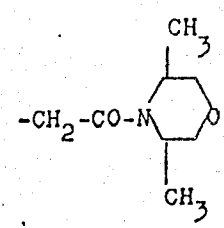

and X denotes an anion ($Cl^-$, $Br^-$, methyl sulfate), have a herbicidal action superior to that of their individual components.

Active ingredients $a$ to $b$ may be applied in amounts of 0.5 to 5 kg per hectare.

The weight ratio of $a : b$ is from 5:1 to 1:5, preferably from 3:1 to 1:3.

The compositions of the invention are suitable for controlling unwanted plants, e.g. dicotyledonous seed weeds, monocotyledonous grassy seed weeds and Cyperaceae in crops such as cereals, rice, soybeans, Indian corn, potatoes, peas, and beans.

The compositions may be applied to the loci of the plants, pre- and/or postemergence.

The agents according to the invention may be used as solutions, emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

EXAMPLE I

In the greenhouse the plants and the soil are treated prior to the emergence of beet (Beta vulgaris) and potatoes (Solanum tuberosum) and after the emergence of wheat (Triticum aestivum) and the unwanted plants green foxtail (Setaria viridis), giant foxtail (Setaria faberii), barnyard grass (Echinochloa crus-galli), slender foxtail (Alopecurus myosuroides), silky bent grass (Apera spica venti), perennial ryegrass (Lolium perenne), bluegrass (Poa trivialis), catchweed bedstraw (Galium aparine), wild mustard (Sinapis arvensis), chamomile (Matricaria chamomilla) and common lambsquarters (Chenopodium album) are treated with the following amounts of the following individual active ingredients and compositions thereof:

| | | |
|---|---|---|
| I | 1,1'-dimethyl-4,4'-dipyridylium-di-(methyl sulfate) | 0.3 kg per hectare; |
| II | 1,1'-di-(3,5-dimethylmorpholinecarbonylmethyl)-4,4'-dipyridylium dichloride, | 0.5 kg per hectare; |
| III | 1,1'-ethylene-2,2'-dipyridylium dibromide, | 0.3 kg per hectare; |
| IV | 3-isopropyl-2,1,3-benzothiadiazinone-(4)-2,2-dioxide, | 0.5 kg per hectare; |
| I + IV: | 0.3 + 0.5 kg per hectare; | |
| II + IV: | 0.5 + 0.5 kg per hectare; | |
| III + IV: | 0.3 + 0.5 kg per hectare. | |

After 10 to 14 days it was ascertained that the compositions had a better herbicidal action than their individual components, combined with the same good crop plant compatibility.

The results are given below:

| Active ingredient kg/ha | I 0.3 | II 0.5 | III 0.3 | IV 0.5 | I + IV 0.3 + 0.5 | II + IV 0.5 + 0.5 | III + IV 0.3 + 0.5 |
|---|---|---|---|---|---|---|---|
| Beta vulgaris | 10 | 0 | 0 | 0 | 0 | 0 | 0 |
| Solanum tuberosum | 0 | 0 | 0 | 0 | 0 | 0 | 0 |
| Triticum aestivum | — | 10 | — | 0 | — | 5 | 5 |
| Setaria viridis | 40 | 25 | 30 | 5 | 90 | 80 | 85 |
| Setaria faberii | 40 | 30 | 35 | 5 | 95 | 80 | 85 |
| Echinochloa crus-galli | 35 | 25 | 30 | 0 | 85 | 75 | 80 |
| Alopecurus myosuroides | 40 | 30 | 35 | 5 | 80 | 70 | 75 |
| Apera spica venti | 50 | 40 | 45 | 10 | 100 | 90 | 95 |
| Lolium perenne | 35 | 25 | 30 | 0 | 80 | 70 | 70 |
| Poa trivialis | 40 | 30 | 35 | 5 | 85 | 75 | 80 |
| Calium aparine | 35 | 30 | 30 | 35 | 90 | 80 | 80 |
| Matricaria chamomilla | 40 | 35 | 35 | 35 | 95 | 80 | 85 |
| Sinapis arvensis | 45 | 40 | 45 | 40 | 100 | 100 | 100 |
| Chenopodium album | 45 | 40 | 40 | 45 | 100 | 100 | 100 |

0 = no damage
100 = complete destruction

EXAMPLE 2

In the greenhouse, various plants were treated at a height of from 3 to 18 cm with the following amounts of the following individual active ingredients and compositions thereof as emulsions, dispersion, suspensions or aqueous solutions:

I 3-isopropyl-2,1,3-benzothiadiazinone-(4)-2,2-dioxide;

II 3-isopropyl-2,1,3-benzothiadiazinone-(4)-2,2-dioxide, sodium salt;

III 3-isopropyl-2,1,3-benzothiadiazinone-(4)-2,2-dioxide, dimethylamine salt;

IV 3-isopropyl-2,1,3-benzothiadiazinone-(4)-2,2-dioxide, diethanolamine salt;

V 1,1-di-(3,5-dimethylmorpholinecarbonylmethyl)-4,4'-dipyridylium dichloride;

VI 1,1-di-(diethylcarbamoylmethyl)-4,4'-dipyridylium dichloride; each at rates of 0.5, 0.75, 1 and 1.5 kg/ha; I+V, II+V, III+V, IV+V, I+VI, II+VI, III+VI and IV+VI, each at rates of 0.5+1, 1+0.5 and 0.75+0.75 kg/ha.

After 2 to 3 weeks it was ascertained that the compositions had a better herbicidal action than their components, combined with the same crop plant compatibility.

The results are given below:

| Active ingredient kg/ha | I 0.5 | I 0.75 | I 1 | I 1.5 | II 0.5 | II 0.75 | II 1 | II 1.5 | III 0.5 | III 0.75 | III 1 | III 1.5 | IV 0.5 | IV 0.75 | IV 1 | IV 1.5 | V 0.5 | V 0.75 | V 1 | V 1.5 |
|---|---|---|---|---|---|---|---|---|---|---|---|---|---|---|---|---|---|---|---|---|
| Crop plants: | | | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 7 | 10 | 15 | 20 | |
| Hordeum vulgare | 0 | 0 | 0 | 0 | 0 | 0 | 0 | 0 | 0 | 0 | 0 | 0 | 0 | 0 | 0 | 5 | 10 | 12 | 20 | |
| Secale cereale | 0 | 0 | 0 | 0 | 0 | 0 | 0 | 0 | 0 | 0 | 0 | 0 | 0 | 0 | 0 | 7 | 11 | 15 | 24 | |
| Unwanted plants: | | | | | | | | | | | | | | | | | | | | |
| Galium aparine | 30 | 35 | 40 | 60 | 30 | 40 | 45 | 60 | 28 | 40 | 50 | 60 | 35 | 45 | 60 | 67 | 30 | 47 | 58 | 65 |
| Alopecurus myosuroides | 2 | 5 | 5 | 10 | 3 | 8 | 12 | 15 | 5 | 7 | 10 | 16 | 4 | 7 | 12 | 15 | 30 | 35 | 42 | 50 |

| Active ingredient kg/ha | VI 0.5 | VI 0.75 | VI 1 | VI 1.5 | I+V 0.5/1 | I+V 1/0.5 | I+V 0.75/0.75 | II+V 0.5/1 | II+V 1/0.5 | II+V 0.75/0.75 | III+V 0.5/1 | III+V 1/0.5 | III+V 0.75/0.75 | IV+V 0.5/1 | IV+V 1/0.5 | IV+V 0.75/0.75 | I+VI 0.5/1 | I+VI 1/0.5 | I+VI 0.75/0.75 |
|---|---|---|---|---|---|---|---|---|---|---|---|---|---|---|---|---|---|---|---|
| Crop plants: | | | | | | | | | | | | | | | | | | | |
| Triticum aestivum | 0 | 0 | 0 | 0 | 15 | 7 | 10 | 15 | 7 | 10 | 15 | 7 | 10 | 15 | 7 | 10 | 0 | 0 | 0 |
| Hordeum vulgare | 0 | 0 | 0 | 0 | 12 | 5 | 10 | 12 | 5 | 10 | 12 | 5 | 10 | 12 | 5 | 10 | 0 | 0 | 0 |
| Secale cereale | 0 | 0 | 0 | 0 | 15 | 7 | 11 | 15 | 7 | 11 | 15 | 7 | 11 | 15 | 7 | 11 | 0 | 0 | 0 |
| Unwanted plants: | | | | | | | | | | | | | | | | | | | |
| Galium aparine | 20 | 25 | 34 | 40 | 100 | 100 | 100 | 100 | 100 | 100 | 100 | 100 | 100 | 100 | 100 | 100 | 100 | 98 | 97 |
| Alopecurus myosuroides | 40 | 45 | 50 | 60 | 90 | 80 | 85 | 87 | 80 | 85 | 94 | 80 | 86 | 90 | 82 | 86 | 95 | 90 | 94 |

| Active ingredient kg/ha | II+VI 0.5/1 | II+VI 1/0.5 | II+VI 0.75/0.75 | III+VI 0.5/1 | III+VI 1/0.5 | III+VI 0.75/0.75 | IV+VI 0.5/1 | IV+VI 1/0.5 | IV+VI 0.75/0.75 |
|---|---|---|---|---|---|---|---|---|---|
| Crop plants: | | | | | | | | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Unwanted plants: | | | | | | | | | |
| Galium aparine | 100 | 100 | 100 | 97 | 100 | 100 | 100 | 100 | 100 |
| Alopecurus myosuroides | 95 | 90 | 96 | 98 | 90 | 94 | 96 | 90 | 95 |

0 = no damage
100 = complete destruction

EXAMPLE 3

In the greenhouse, various plants were treated at a height of from 3 to 18 cm with the following amounts of the following individual active ingredients and compositions thereof as emulsions, dispersions, suspensions or aqueous solutions:

I 3-isopropyl-2,1,3-benzothiadiazinone-(4)-2,2-dioxide;
II 3-isopropyl-2,1,3-benzothiadiazinone-(4)-2,2-dioxide, sodium salt;
III 3-isopropyl-2,1,3-benzothiadiazinone-(4)-2,2-dioxide, dimethylamine salt;
IV 3-isopropyl-2,1,3-benzothiadiazinone-(4)-2,2-dioxide, diethanolamine salt;
V 1,1-di-(3,5-dimethylmorpholinecarbonylmethyl)-4,4'-dipyridylium dichloride;
VI 1,1-di-(diethylcarbamoylmethyl)-4,4'-dipyridylium dichloride; each at rates of 0.25, 0.5, 0.75, 1, 1.25 and 1.5 kg/ha;

I+V, II+V, III+V, IV+V, I+VI, II+VI, III+VI and IV+VI, each at rates of 0.75+0.75, 0.25+1.25, 1.25+0.25, 0.25+0.75, 0.75+0.25 and 0.5+0.5 kg/ha.

After 2 to 3 weeks it was ascertained that the compositions had a better herbicidal action than their components, combined with the same crop plant compatibility.

The results are given below:

| Active ingredient kg/ha | I | | | | | | II | | | | | | III | | | | | |
|---|---|---|---|---|---|---|---|---|---|---|---|---|---|---|---|---|---|---|
| | 0.25 | 0.5 | 0.75 | 1 | 1.25 | 1.5 | 0.25 | 0.5 | 0.75 | 1 | 1.25 | 1.5 | 0.25 | 0.5 | 0.75 | 1 | 1.25 | 1.5 |
| Crop plants: | | | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 | 0 | 0 |
| Unwanted plants: | | | | | | | | | | | | | | | | | | |
| Galium aparine | 20 | 30 | 35 | 40 | 55 | 60 | 15 | 30 | 40 | 45 | 55 | 60 | 20 | 28 | 40 | 50 | 55 | 60 |
| Alopecurus myosuroides | 0 | 2 | 5 | 5 | 7 | 10 | 0 | 3 | 8 | 12 | 15 | 15 | 0 | 5 | 7 | 10 | 14 | 16 |

0 = no damage
100 = complete destruction

| Active ingredient kg/ha | IV | | | | | | V | | | | | | VI | | | | | |
|---|---|---|---|---|---|---|---|---|---|---|---|---|---|---|---|---|---|---|
| | 0.25 | 0.5 | 0.75 | 1 | 1.25 | 1.5 | 0.25 | 0.5 | 0.75 | 1 | 1.25 | 1.5 | 0.25 | 0.5 | 0.75 | 1 | 1.25 | 1.5 |
| Crop plants: | | | | | | | | | | | | | | | | | | |
| Triticum aestivum | 0 | 0 | 0 | 0 | 0 | 0 | 5 | 7 | 10 | 15 | 18 | 20 | 0 | 0 | 0 | 0 | 0 | 0 |
| Hordeum vulgare | 0 | 0 | 0 | 0 | 0 | 0 | 2 | 5 | 10 | 12 | 15 | 20 | 0 | 0 | 0 | 0 | 0 | 0 |
| Secale cereale | 0 | 0 | 0 | 0 | 0 | 0 | 3 | 7 | 11 | 15 | 20 | 24 | 0 | 0 | 0 | 0 | 0 | 0 |
| Unwanted plants: | | | | | | | | | | | | | | | | | | |
| Galium aparine | 25 | 35 | 45 | 60 | 65 | 67 | 15 | 30 | 47 | 58 | 60 | 65 | 10 | 20 | 25 | 35 | 38 | 40 |
| Alopecurus myosuroides | 0 | 4 | 7 | 12 | 15 | 15 | 10 | 30 | 35 | 42 | 48 | 50 | 30 | 40 | 45 | 50 | 55 | 60 |

| Active ingredient kg/ha | I+V | | | | | | II+V | | | | | |
|---|---|---|---|---|---|---|---|---|---|---|---|---|
| | 0.75 / 0.75 | 0.25 / 1.25 | 1.25 / 0.25 | 0.25 / 0.75 | 0.75 / 0.25 | 0.5 / 0.5 | 0.75 / 0.75 | 0.25 / 1.25 | 1.25 / 0.25 | 0.25 / 0.75 | 0.75 / 0.25 | 0.5 / 0.5 |
| Crop plants: | | | | | | | | | | | | |
| Triticum aestivum | 10 | 18 | 5 | 10 | 5 | 7 | 10 | 18 | 5 | 10 | 5 | 7 |
| Hordeum vulgare | 10 | 15 | 2 | 10 | 2 | 5 | 10 | 15 | 2 | 10 | 2 | 5 |
| Secale cereale | 11 | 20 | 3 | 11 | 3 | 7 | 11 | 20 | 3 | 11 | 3 | 7 |
| Unwanted plants: | | | | | | | | | | | | |
| Galium aparine | 100 | 100 | 100 | 100 | 90 | 100 | 100 | 100 | 100 | 100 | 95 | 100 |
| Alopecurus myosuroides | 85 | 90 | 60 | 75 | 60 | 72 | 85 | 90 | 65 | 75 | 60 | 75 |

| Active ingredient kg/ha | III+V | | | | | | IV+V | | |
|---|---|---|---|---|---|---|---|---|---|
| | 0.75 / 0.75 | 0.25 / 1.25 | 1.25 / 0.25 | 0.25 / 0.75 | 0.75 / 0.25 | 0.5 / 0.5 | 0.75 / 0.75 | 0.25 / 1.25 | 1.25 / 0.25 |
| Crop plants: | | | | | | | | | |
| Triticum aestivum | 10 | 18 | 5 | 10 | 5 | 7 | 10 | 18 | 5 |
| Hordeum vulgare | 10 | 15 | 2 | 10 | 2 | 5 | 10 | 15 | 2 |
| Secale cereale | 11 | 20 | 3 | 11 | 3 | 7 | 11 | 20 | 3 |
| Unwanted plants: | | | | | | | | | |
| Galium aparine | 100 | 100 | 100 | 100 | 97 | 98 | 100 | 100 | 100 |
| Alopecurus myosuroides | 86 | 90 | 65 | 75 | 60 | 75 | 86 | 96 | 70 |

| Active ingredient kg/ha | IV+V | | | I+VI | | | | | | II+VI | | | | | |
|---|---|---|---|---|---|---|---|---|---|---|---|---|---|---|---|
| | 0.25 / 0.75 | 0.75 / 0.25 | 0.5 / 0.5 | 0.75 / 0.75 | 0.25 / 1.25 | 1.25 / 0.25 | 0.25 / 0.75 | 0.75 / 0.25 | 0.5 / 0.5 | 0.75 / 0.75 | 0.25 / 1.25 | 1.25 / 0.25 | 0.25 / 0.75 | 0.75 / 0.25 | 0.5 / 0.5 |
| Crop plants: | | | | | | | | | | | | | | | |
| Triticum aestivum | 10 | 5 | 7 | 0 | 0 | 0 | 0 | 0 | 0 | 0 | 0 | 0 | 0 | 0 | 0 |
| Hordeum vulgare | 10 | 2 | 5 | 0 | 0 | 0 | 0 | 0 | 0 | 0 | 0 | 0 | 0 | 0 | 0 |
| Secale cereale | 11 | 3 | 7 | 0 | 0 | 0 | 0 | 0 | 0 | 0 | 0 | 0 | 0 | 0 | 0 |
| Unwanted plants: | | | | | | | | | | | | | | | |
| Galium aparine | 100 | 100 | 100 | 100 | 100 | 100 | 85 | 87 | 90 | 100 | 95 | 100 | 80 | 90 | 90 |
| Alopecurus myosuroides | 78 | 60 | 75 | 94 | 96 | 80 | 85 | 77 | 85 | 96 | 95 | 86 | 85 | 80 | 85 |

| Active ingredient kg/ha | III+VI | | | | | | IV+VI | | | | | |
|---|---|---|---|---|---|---|---|---|---|---|---|---|
| | 0.75 / 0.75 | 0.25 / 1.25 | 1.25 / 0.25 | 0.25 / 0.75 | 0.75 / 0.25 | 0.5 / 0.5 | 0.75 / 0.75 | 0.25 / 1.25 | 1.25 / 0.25 | 0.25 / 0.75 | 0.75 / 0.25 | 0.5 / 0.5 |
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 100 | 100 | 100 | 85 | 90 | 90 | 100 | 100 | 100 | 90 | 95 | 95 |
| Alopecurus myosuroides | 94 | 96 | 85 | 85 | 80 | 87 | 95 | 96 | 85 | 87 | 80 | 85 |

I claim:

1. A herbicide composition comprising an inert carrier having dispersed therein a herbicidally effective amount of a mixture consisting essentially of
a. a compound of the formula

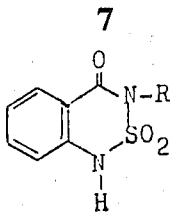

where R denotes lower alkyl of a maximum of 4 carbon atoms, or an alkali metal, alkaline earth metal, ammonium, lower hydroxyalkylammonium, lower alkylammonium or hydrazine salt thereof, and b. a compound of the formula

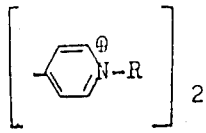 

where R denotes the radical

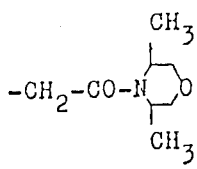

and X denotes an anion in a weight ratio of a:b of 3:1 to 1:3.

2. A herbicide composition as claimed in claim 1 wherein compound (b) is 1,1'-di-(3,5-dimethylmorpholinecarbonylmethyl)-4,4'-dipyridylium dichloride.

3. A herbicide composition as claimed in claim 1 wherein X is $Cl^-$, $Br^-$ or methyl sulfate.

4. A process for controlling growth of unwanted plants among crop plants which comprises applying to the locus of the plants a herbicidally effective amount of a mixture of herbicides consisting essentially of a. a compound of the formula where R denotes lower alkyl of a maximum of 4 carbon atoms, or an alkali metal, alkaline earth metal, ammonium, lower hydroxyalkylammonium, lower alkylammonium or hydrazine salt thereof, and b. a compound of the formula

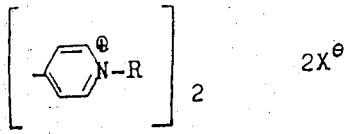

where R denotes the radical and X denotes an anion in a weight ratio of a:b of 3:1 to 1:3.

5. A process as claimed in claim 4 wherein compound (b) is 1,1'-di-(3,5-dimethylmorpholinecarbonylmethyl)-4,4'-dipyridylium dichloride.

6. A process as claimed in claim 4 wherein X is $Cl^-$, $Br^-$ or methyl sulfate.

7. A herbicide composition as claimed in claim 1 wherein R in compound a is isopropyl.

8. A herbicide composition as claimed in claim 1 wherein R in compound a is isopropyl, and said weight ratio is 1:1.

9. A process as claimed in claim 4 wherein R in compound a is isopropyl.

10. A process as claimed in claim 4 wherein R in compound a is isopropyl, and said weight ratio is 1:1.

* * * * *